United States Patent
Katyal et al.

(10) Patent No.: US 8,836,266 B2
(45) Date of Patent: Sep. 16, 2014

(54) SMALL MOTOR CONTROLLER

(75) Inventors: Kapil D Katyal, Chevy Chase, MD (US); Matthew P. Para, Laurel, MD (US); Andrew J. Harris, Columbia, MD (US); Harry A. Eaton, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 180 days.

(21) Appl. No.: 13/551,846

(22) Filed: Jul. 18, 2012

(65) Prior Publication Data

US 2014/0025182 A1 Jan. 23, 2014

(51) Int. Cl.
*G05B 19/29* (2006.01)
*G05B 19/416* (2006.01)

(52) U.S. Cl.
CPC .................................. *G05B 19/416* (2013.01)
USPC ............ 318/601; 318/600; 318/560; 318/567

(58) Field of Classification Search
CPC ........................... G05B 19/416; G05B 19/404
USPC .................... 318/601, 600, 560, 567
See application file for complete search history.

(56) References Cited

U.S. PATENT DOCUMENTS

| | | | |
|---|---|---|---|
| 4,329,636 A * | 5/1982 | Uchida et al. | 318/721 |
| 5,187,417 A | 2/1993 | Minnich et al. | |
| 5,637,974 A | 6/1997 | McCann | |
| 5,677,605 A | 10/1997 | Cambier et al. | |
| 6,249,101 B1 * | 6/2001 | Viti et al. | 318/560 |
| 6,949,903 B2 | 9/2005 | Berroth et al. | |
| 7,072,778 B2 * | 7/2006 | Swanson | 702/57 |
| 7,579,799 B2 | 8/2009 | Robichaux et al. | |
| 7,714,571 B2 | 5/2010 | Pirozzi et al. | |
| 7,786,686 B2 | 8/2010 | D'Angelo et al. | |
| 7,800,325 B2 | 9/2010 | Song et al. | |
| 7,810,362 B2 | 10/2010 | Harwood et al. | |
| 7,893,579 B2 | 2/2011 | Rudel et al. | |
| 8,390,277 B2 * | 3/2013 | Takeuchi | 324/207.25 |

FOREIGN PATENT DOCUMENTS

JP   2000083395 A   3/2000

* cited by examiner

*Primary Examiner* — David S Luo
(74) *Attorney, Agent, or Firm* — Noah J. Hayward (57) ABSTRACT

A small motor controller (SMC) system includes a motor configured to control a position of a rotor, a sensor configured to detect position information of the rotor by detecting a feature on the rotor, the sensor including a detection zone having a first side and a second side, and a motor control unit. The motor control unit is configured to determine a position of the rotor corresponding to one of the first side of the detection zone and the second side of the detection zone based on whether the feature on the rotor is detected crossing the first side or the second side, respectively.

16 Claims, 4 Drawing Sheets

SMALL MOTOR CONTROLLER

STATEMENT OF GOVERNMENTAL INTEREST

This invention was made with government support under contract number N66001-06-C-8005 awarded by the Defense Advanced Research Projects Agency (DARPA). The government has certain rights in the invention.

BACKGROUND

The present disclosure relates to a small motor controller, and more specifically, to a small motor controller and programs to control a small motor which determine position information of a rotor or motor and control a position of the rotor or motor.

Small motor controllers (SMCs) are used in various applications to control the operation of small motors. Motors may take many forms including a magnetizable element, such as a coil, and a magnetic element, such as a permanent magnet connected to a rotor. An SMC may control rotation of the rotor by generating controls signals to energize the coil, causing a magnetic field interaction between the coil and the permanent magnet, and causing the rotor to rotate.

In some applications a user or program needs to know the position of a rotor, and hardware may be provided, such as a high-resolution encoder, to determine the rotor position. In addition, an SMC may use a sensor output from a small motor to generate a motor control signal to control the small motor. However, since processing the sensor output from the sensor takes time, a motor control signal generated by the SMC based on the sensor output corresponds to outdated information about the small motor.

SUMMARY

According to one embodiment of the present invention, a small motor controller (SMC) system includes a motor configured to control a position of a rotor, a sensor configured to detect position information of the rotor by detecting a feature on the rotor, the sensor including a detection zone having a first side and a second side, and a motor control unit. The motor control unit is configured to determine a position of the rotor corresponding to one of the first side of the detection zone and the second side of the detection zone based on whether the feature on the rotor is detected crossing the first side or the second side, respectively.

According to another embodiment of the present invention, a non-transitory computer-readable medium has stored thereon a computer program, which, when executed by a computer, performs a method on the computer. The method comprises receiving a sensor output signal, determining whether the sensor output signal corresponds to a feature of a rotor entering a sensing zone of a sensor from a first side or a second side opposite the first side, and determining a position of the rotor corresponding to one of the first side of the sensing zone and the second side of the sensing zone based on whether the feature on the rotor is detected adjacent to the first side or the second side, respectively.

According to yet another embodiment of the present invention, a prosthetic limb includes a joint including a motor to bend the joint, a sensor configured to detect position information of the motor by detecting a feature on a rotor of the motor, the sensor including a detection zone having a first side and a second side, and a motor control unit configured to a position of the rotor corresponding to one of the first side of the detection zone and the second side of the detection zone based on whether the feature on the rotor is detected crossing the first side or the second side, respectively.

According to yet another embodiment of the present invention, a method includes receiving a sensor output signal, determining whether the sensor output signal corresponds to a feature of a rotor entering a sensing zone of a sensor from a first side or a second side opposite the first side, and determining a position of the rotor corresponding to one of the first side of the sensing zone and the second side of the sensing zone based on whether the feature on the rotor is detected adjacent to the first side or the second side, respectively.

According to yet another embodiment of the present invention a small motor controller system including a motor configured to control a position of a rotor, a sensor configured to detect position information of the rotor, and a motor control unit configured to receive from the sensor a sensor output signal, to calculate a time for processing the sensor output signal, and to adjust an output motor control signal to the motor based on the calculated time for processing the sensor output signal.

Additional features and advantages are realized through the techniques of exemplary embodiments of the present invention. Other embodiments and aspects of the invention are described in detail herein and are considered a part of the claimed invention. For a complete understanding of the exemplary embodiments of the invention with the advantages and the features described herein, refer to the description and to the drawings.

BRIEF DESCRIPTION OF THE DRAWINGS

The subject matter which is regarded as the invention is particularly pointed out and distinctly claimed in the claims at the conclusion of the specification. The forgoing and other features, and advantages of preferred and/or exemplary embodiments the invention will become even more readily apparent from the following detailed description, taken in conjunction with the accompanying drawings, in which:

DETAILED DESCRIPTION

Embodiments of the present disclosure relate to controlling a small motor and in particular a small motor in a prosthetic limb. The small motor may control bending of the limb, such as at a joint in the limb. In some embodiments, characteristics of a position detection sensor may be used to provide information regarding a position of a rotor or a rotation direction of a rotor, without requiring additional sensors or encoders to determine the position or rotation direction. Increasing the precision of the position information of the rotor results in increasing the torque of the motor. In some embodiments, a processing time of sensor signals may be calculated and output motor control signals may be adjusted based on the processing time. Accordingly, a small motor may be monitored and controlled with precision and with a minimal number of components.

Figure 1:
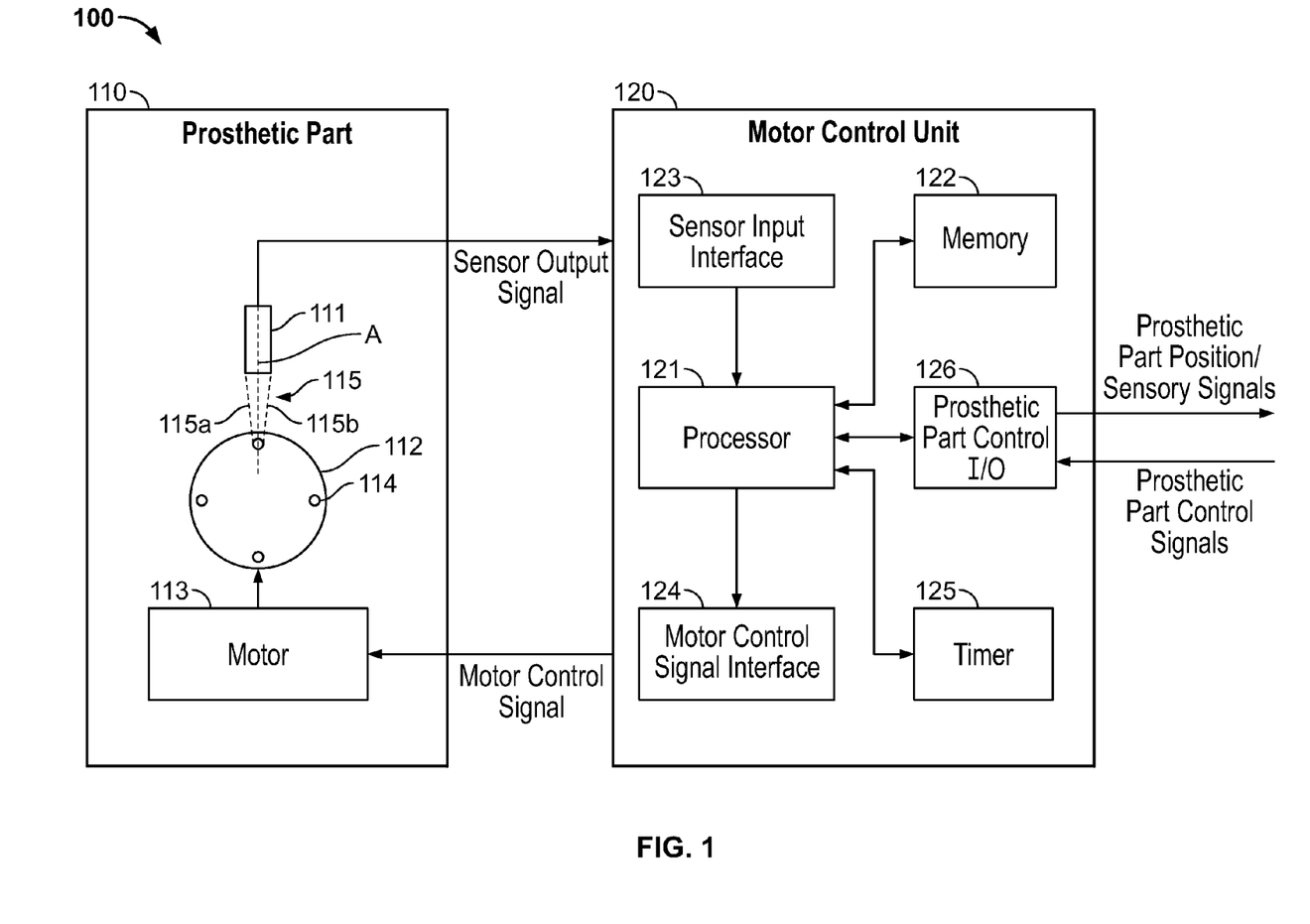
FIG. 1 illustrates a prosthetic limb control system according to an embodiment of the invention.

With reference now to FIG. 1, a prosthetic limb control system 100 includes a prosthetic part 110 and a motor control unit 120, such as a small motor controller (SMC). The prosthetic part 110 includes a sensor 111, a rotor 112, and a motor 113. The sensor 111 detects a characteristic of the rotor 112, such as a position of the rotor 112. In one embodiment, the sensor 111 detects features 114 on the rotor 112. The features 114 may correspond to predetermined locations on the rotor 112 to provide location information from which position information of the rotor 112 may be derived. In one embodiment, the sensor 111 is a Hall-effect sensor and the features 114 are magnets formed in or attached to the rotor 112. In other embodiments, the features 114 may be protrusions, recesses, portions of the rotor 112 formed of different materials than the rest of the rotor 112, circuits or electrical elements, or any other type of distinctive feature 114 detectable by a sensor 111 to obtain characteristic information about position or movement of the rotor 112.

In one embodiment, the rotor 112 is part of the motor 113. For example, the motor 113 may be a brushless motor including magnetizable coils surrounding the rotor 112. A motor control signal may control a current supplied to the magnetizable coils to control a magnetic field around the coil, and to thereby control a rotation speed and/or direction of the rotor 112. In another embodiment, the motor 113 is separate from the rotor 112 and drives the rotor 112 mechanically, magnetically, or by any other force.

The motor control unit 120 includes a processor 121, a sensor input interface 123 to receive a sensor output signal from the sensor 111, and a motor control signal interface 124 configured to output one or more motor control signals to the motor 113 to control operation of the motor 113 and the rotor 112. The motor control unit 120 may further include memory 122 for storing programs to control the motor 113 and/or data generated by the sensor 111. The motor control unit 120 may also include a prosthetic part control I/O 126 configured to receive from a prosthetic part controller (not shown) a prosthetic part control signal, and to output to the prosthetic part controller position information and/or sensory information from the prosthetic part 110.

In one embodiment, the prosthetic part 110 is a prosthetic digit or limb, such as a finger, hand, arm, toe, foot, or leg. A user may interact with the prosthetic part controller by physical buttons or levers, visual-interface controls, nerve-interface controls, or other controls to control the prosthetic part 110. For example, a user may control the motor 113 to rotate the rotor 112 to bend a joint of the prosthetic part 110. The prosthetic part controller may provide the prosthetic part control signals to the prosthetic part control I/O 126 and to the processor 121. The processor 121 may generate a motor control signal based on the prosthetic part control signal and may output the motor control signal to the motor 113 via the motor control signal interface 124.

As the rotor 112 rotates in response to the motor control signal or in response to external forces on the prosthetic part 110, the sensor 111 generates sensor output signals to the sensor input interface 123, and the sensor input interface 123 outputs the sensor output signal to the processor 121. The processor 121 may adjust the motor control signal to the motor 112 based on the sensor output signal to maintain the rotor 112 at a predetermined position, or to rotate the rotor 112 at a predetermined rate or in a predetermined direction, as indicated by the prosthetic part control signals from the prosthetic part controller.

The processor 121 may output prosthetic part position information and/or sensory signals to the prosthetic part controller via the prosthetic part control I/O 126. The position information and/or sensory signals may correspond to position information of the rotor 112, of portions of the prosthetic part 110, of sensations of movement, temperature, pressure, pain, or other position information or sensory signals.

In embodiments of the present disclosure, the sensor 111 senses a feature 114 of the rotor 112 within a sensing field 115. The sensing field 115 may also be referred to as a detection zone, a sensing zone, or a detection field. The sensing field 115 has a first side 115a and a second side 115b, and the sensing field 115 encompasses the area between the first side 115a, the second side 115b, the sensor 111 and a portion of the rotor 112 including one or more features 114. The sensing field 115 is centered about a center axis A that is aligned along a length of the sensor 111 and a center of the sensing field 115 traversing both the sensor 111 and the rotor 112.

When the rotor 112 rotates in a clockwise direction, a feature 114 of the rotor may enter the sensory field 115 from the first side 115a and may exit from the second side 115b. Conversely, when the rotor 112 rotates in a counter-clockwise direction, a feature 114 of the rotor may enter the sensory field 115 from the second side 115b and may exit the sensing field 115 from the first side 115a. A precise position of the rotor may be determined by detecting when the feature 114 crosses the first side 115a, a center axis A, and the second side 115b of the sensing field 115. In other words, the first side 115a and second side 115b of the sensing field 115 are used as additional sensing points, without creating a need for additional circuitry, to detect a position of the rotor 112. In addition, a rotation direction of the rotor 112 may be stored in memory or calculated based on the detection of subsequent features 114, or the first side 115a or second side 115b may be used to determine a clock-wise or counter-clockwise rotation of the rotor 112.

FIGS. 4 and 5A-5C illustrate a rotor 112 and position detection according to an embodiment of the invention. Referring to FIGS. 1, 4, and 5A-5C, the rotor 112 includes a plurality of features 114a-114h detectable by a sensor 111. The sensor 111 generates a sensing field 115 having a first side 115a, a second side 115b, and a center axis A located equidistant from the first side 115a and the second side 115b. Although FIGS. 1, 4, and 5A-5C illustrate a sensing field 115 having a conical shape that narrows towards the rotor 112, the sensing field 115 may include any shape.

The first side 115a may cross the rotor 112 surface at a point 112a, the second side 115b may cross the rotor 112 surface at a point 112b, and the center axis A may cross the rotor 112 surface at a point 112c. The first and second points 112a and 112b may each be an arc length al from the point 112c. In one embodiment, the arc length al is half of a length between the centers of two adjacent features 114, such as features 114a and 114b. In such an embodiment, the sensing capability of the sensor 111 in determining a location of the rotor may be effectively doubled, since a center of each feature 114 may be detected and a point mid-way between two features 114 may also be detected. Embodiments of the present invention encompass any arc length al different than a distance between the centers of two adjacent features 114. In other words, embodiments of the present invention encompass any arc length al which would cause the sensor 111 to generate information about additional positions of the rotor other than the centers of the features 114 based on the first side 115a and the second side 115b of the sensing field 115.

Figure 5A:
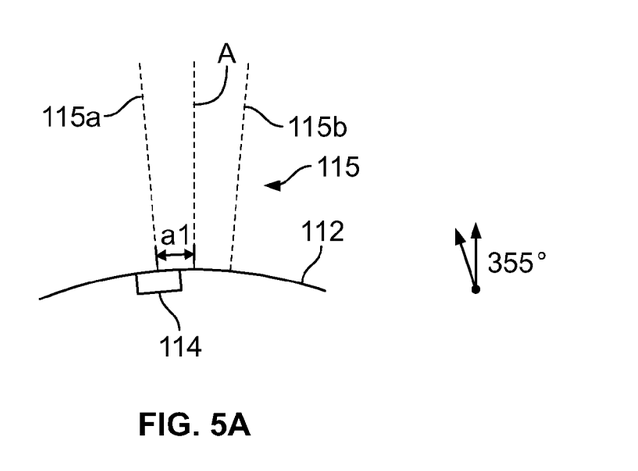
FIGS. 5A to 5C illustrate position detection of a rotor according to an embodiment of the invention.
Figure 5B:
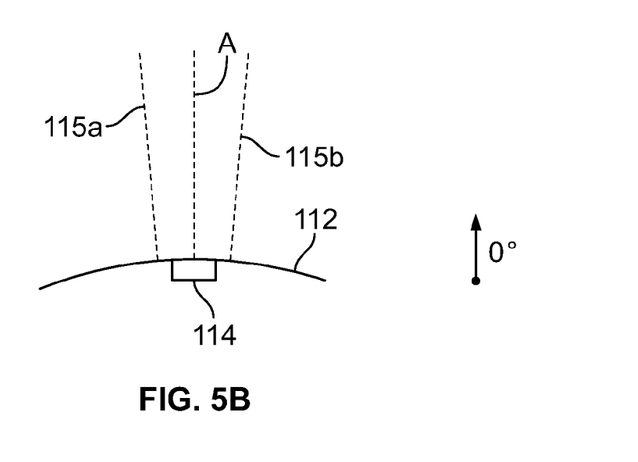
Figure 5C:
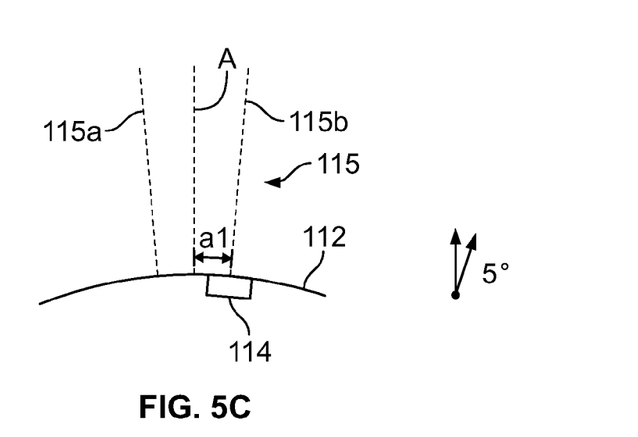

As illustrated in FIG. 5A, when the feature 114 crosses or is adjacent to the first side 115a, a first signal or form may be generated by the sensor 111. Accordingly, the processor 121 may determine that the rotor 112 is in a position having the feature 114 located where the first side 115a of the sensing field 115 contacts the rotor 112. As illustrated in FIG. 5B, when the feature 114 crosses or is adjacent to the first side center axis A, a second signal or form may be generated by the sensor 111. Accordingly, the processor 121 may determine that the rotor 112 is in a position having the feature 114 located where the center axis A of the sensing field 115 contacts the rotor 112. As illustrated in FIG. 5C, when the feature 114 crosses or is adjacent to the second side 115b, a third signal or form may be generated by the sensor 111. Accordingly, the processor 121 may determine that the rotor 112 is in a position having the feature 114 located where the second side 115b of the sensing field 115 contacts the rotor 112.

When the position of FIG. 5B is considered a center position, or a position where the rotor is at a rotation angle of 0 degrees, the processor 121 may determine that the rotor is a position of 355 degrees when the rotor 112 is in the position indicated in FIG. 5A and an arc length al between the center axis A and the first side 115a of the sensing field 115 is 5 degrees. Similarly, the processor 121 may determine that the rotor is a position of 5 degrees when the rotor 112 is in the position indicated in FIG. 5C and an arc length al between the center axis A and the second side 115b of the sensing field 115 is 5 degrees.

The sensor 111 may output signals having different forms based on whether the feature 114 is located in line with, or adjacent to, the first side 115a or from the second side 115b, or whether the feature 114 is located along the center axis A. For example, the sensor 111 may output a signal having a first form when the feature 114 enters the sensory field 115 from the first side 115a or is located in-line with or adjacent to the first side 115a. The first form may be, for example, a waveform. The sensor 111 may output a signal having a second form when the feature 114 is located along the center axis A. The second form may be different from the first form in shape, magnitude, frequency, or any other detectable characteristic.

The sensor 111 may further output a signal having a third form when the feature 114 enters the sensory field 115 from the second side 115b, or when the feature 114 is located opposite the second side 115b. In one embodiment, the first form and the third form are waveforms and are mirror images of each other.

The processor 121 may detect whether the first form, second form, or third form is generated, and may determine a precise location or a rotation direction of the rotor 112 based on whether the first form, the second form, or the third form is detected. The different forms generated by the sensor 111 may correspond to different voltage levels, different current levels, different waveforms, different frequencies or any other distinctive sensor output signal.

In embodiments of the present invention, a position of the rotor 112 may be determined at least within a range of a width w1 of a feature 114. For example, if a first form is output by the sensor 111, the processor 121 may determine that at least some portion of the feature 114 is opposite the sensor 111, and that the position of the rotor 112 corresponds to a range within the width w1 of the feature 114. However, embodiments of the present invention encompass levels of accuracy greater than a width of a feature 114 or less than a width of a feature 114 according to sensor 111 characteristics, processor 121 capabilities, feature 114 characteristics, or any other design characteristics of the control system 100.

In embodiments in which the rotor 112 and/or the motor 113 are small in size, such as sufficiently small to fit within a human knuckle or joint, or having a diameter of approximately 1 cm or less, where space is limited, detecting the precise location or the rotation direction of the rotor 112 based on the sensing field 115 may eliminate the need for additional hardware, such as a high-resolution encoder, to determine the precise location or rotation direction of the rotor 112. In other words, embodiments of the present invention include a processor 121 and motor control unit 120 configured to detect a precise location and/or a rotation direction of a rotor 112 and/or motor 113 without the use of a high-resolution encoder.

Although FIG. 1 illustrates the motor control unit 120 as being outside the prosthetic part 110, both the motor control unit 120 may be within a same prosthetic part 110 or prosthetic limb. For example, in one embodiment, the prosthetic part 110 corresponds to a finger of a prosthetic hand or grasping mechanism, and the motor control unit 120 is located within a hand component of the prosthetic hand or grasping mechanism. In another embodiment, the prosthetic part 110 corresponds to a toe or other digit of a prosthetic foot, and the motor control unit 120 is located within the prosthetic foot.

Figure 2:
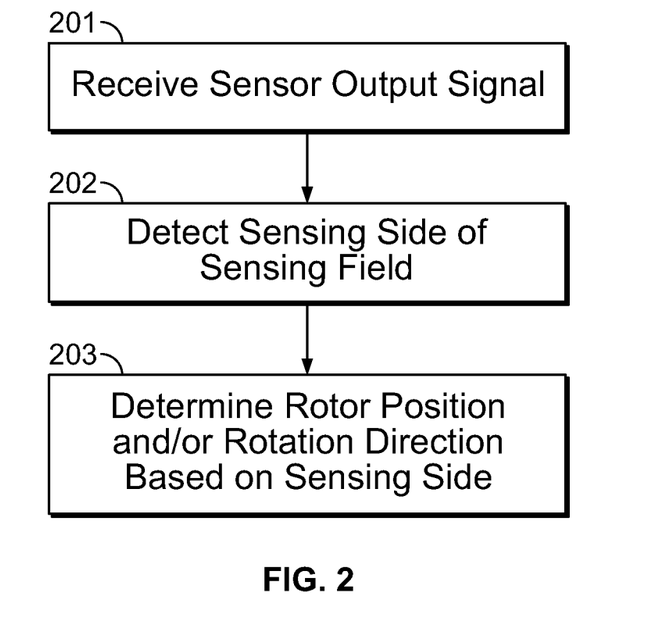
FIG. 2 illustrates a method of detecting a rotor direction according to an embodiment of the invention.

FIG. 2 illustrates a method according to one embodiment of the present invention. In operation 201, a sensor output signal is received from a sensor configured to detect the position of a rotor, such as the sensor 111 of FIG. 1. In operation 202, a sensing side of a sensing field is detected. In particular, it is determined whether a feature of the rotor first crosses or is located along or adjacent to a first side of a sensing field, a second side of the sensing field, or a center axis of the sensing field. The sensing field corresponds to a field in which the sensor is capable of detecting the feature of the rotor.

In operation 203, the precise position of the rotor is determined based on the determination whether a feature of the rotor is located opposite or adjacent to the first side, the second side, or the center axis of the sensing field. In addition, it may be determined whether the rotor is rotating in a clockwise direction or in a counter-clockwise direction based on the determination that the feature of the rotor first entered the sensing field from the first side or from the second side.

Embodiments of the present invention encompass a system including the rotor 112, motor 113, sensor 111 and motor control unit 120 of FIG. 1, or any other system in which a sensor includes a sensing field, and a precise position of an object or a rotation direction or movement direction of an object may be detected by determining a side of the sensing field by which a predetermined feature enters the sensing field. Embodiments of the present invention may be applied in an environment in which the motor 113 and rotor 112 are small components, such as 1 cm or less in diameter, such as in the joint of a prosthetic limb. The motor control unit 120 may also be located within the prosthetic limb, and may also be a small component, such as a component having any length dimension of less than 10 cm.

In one embodiment of the present invention, the processor 121 may generate a motor control signal that compensates for a processing time of one or both of the sensor output signal and the motor control signal. In particular, the processor 121 may receive the sensor output signal to determine a characteristic of the rotor 112, such as a position, rotation direction, or rotation speed of the rotor 112. The processor 121 may compare the characteristic of the rotor 112 to a desired characteristic, such as a characteristic indicated by a prosthetic part control signal and/or a previously-generated motor control signal. The processor 121 may calculate a necessary change needed to adjust the characteristic of the rotor 112 to correspond to the desired characteristic, and the processor 121 may generate a motor control signal corresponding to the necessary change.

Since processing of the sensor output signal and generating a new motor control signal take time to perform, an embodiment of the present invention takes into account the time necessary to process the sensor output signal and generate the new motor control signal when generating the new motor control signal. Processing the sensor output signal may include converting the sensor output signal from one form to another, such as from an analog signal to a digital signal, a signal having one waveform to a signal having another waveform, computing a new motor velocity, or any other conversion. Processing the sensor output signal may also include comparing the sensor output signal to a signal corresponding desired characteristic of the rotor 112 and calculating a necessary change to the motor control signal based on any difference between the sensor output signal and the signal corresponding to the desired characteristic of the rotor 112. Processing the sensor output signal may also include generating a new or adjusted motor control signal based on calculations of the processor to correct the characteristic of the rotor 112.

For example, the sensor output signal may indicate a first rotor 112 position that is different from a desired second rotor 112 position. The processor 121 may calculate a desired change in the motor control signal to correspond to the desired second rotor 112 position and may generate a motor control signal based on the desired second rotor 112 position and the sensed first rotor 112 position. Similarly, the sensor output signal may indicate a first rotor 112 rotation direction, and the processor 121 may calculate a desired change in the motor control signal to correspond to a desired rotor 112 rotation direction.

In an embodiment of the present invention the processor 121 may adjust the motor control signal to account for the time needed to process the sensor output signal. In one embodiment, the processor 121 receives as an input the sensor output signal, converts the sensor output signal, compares the sensor output signal to a desired signal, and calculates the change necessary in the motor control signals to adjust a characteristic of the rotor. In addition, the processor 121 calculates the time necessary to perform the converting, comparing and calculating, and generates a modified or adjusted motor control signal that compensates for the calculated time necessary to perform the converting, comparing, and calculating, as well as transmitting the sensor output signal and a motor control signal.

In one embodiment, the modified or adjusted motor control signal comprises multiple components including an un-modified motor control signal configured to change a characteristic of the rotor 112 by a first amount, and an adjustment portion, such as an increase or decrease in voltage, current, frequency, or modulation of the motor control signal, that is applied to the un-modified portion to account for the time necessary to perform the converting, comparing, and calculating operations, including signal transmission time.

Accounting for the time needed to process the sensor output signal may include extrapolating a future rotor 112 characteristic based on the sensed rotor 112 characteristic. For example, in an embodiment in which the rotor 112 characteristic is a position of the rotor, the presently-sensed position may be compared to at least one previously-sensed position, and a future rotor 112 position may be extrapolated to correspond to a time necessary for the processor 121 to process the sensor output signal. The processor 121 may then generate the motor control signal based on the extrapolated rotor 112 position rather than the sensed rotor 112 position.

In another embodiment in which the rotor 112 characteristic is a rotation speed or rotation direction of the rotor 112, a future rotation speed or rotation direction may be extrapolated based on the presently-sensed rotation speed or direction and at least one previously-sensed rotation speed or direction. Then, a motor control signal may be generated based on the future rotation speed or direction instead of the presently-sensed rotation speed or direction. Although a few examples of rotor 112 characteristics have been provided by way of description, embodiments of the present invention encompass any characteristic corresponding to a position or rotation of the rotor 112.

In one embodiment, calculating the time necessary to perform the converting, comparing and calculating operations based on the sensor output signal includes beginning the timer 125 of the motor control unit 120 upon receipt of the sensor output signal and stopping the timer 125 upon completion of the calculating operation. In another embodiment, the time necessary to perform one or more of the converting, comparing and calculating is predetermined or averaged, and a representative time is stored in memory 122 and accessed by the processor 121 to calculate the time necessary to perform these functions. In one embodiment, part of the time necessary to perform the converting, comparing and calculating is based on a time tracked by the timer 125, and a part is based on a predetermined time stored in memory 122.

Figure 3:
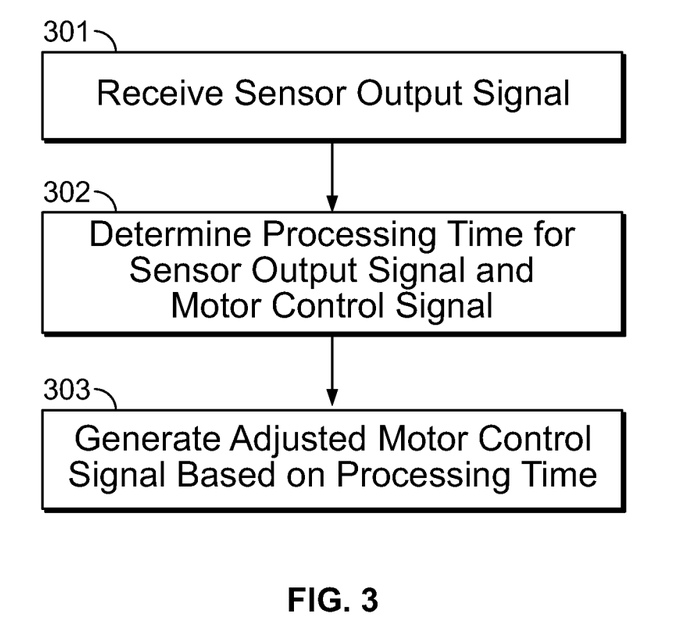
FIG. 3 illustrates a method of adjusting a motor control signal according to an embodiment of the invention.
Figure 4:
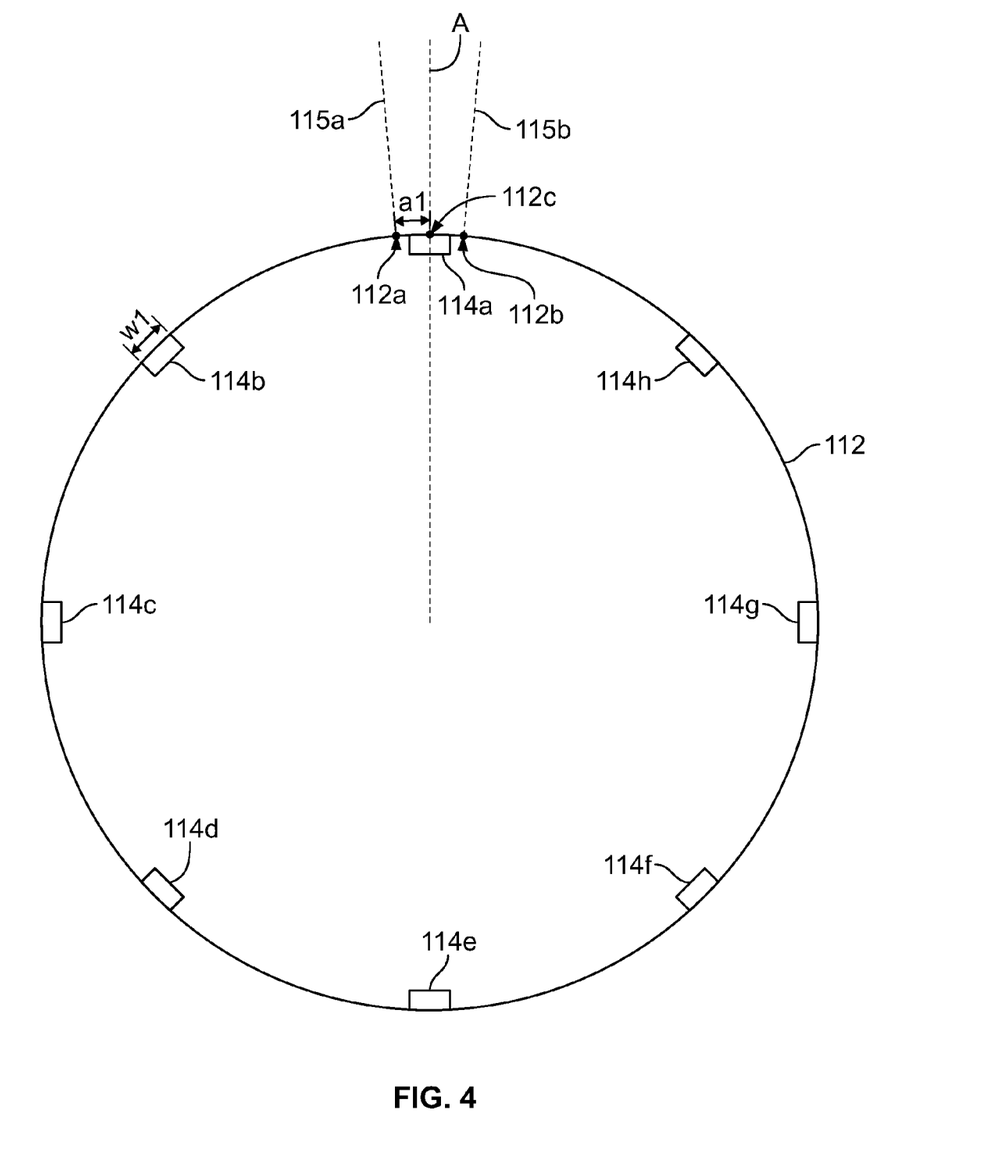
FIG. 4 illustrates a rotor according to an embodiment of the invention.

FIG. 3 illustrates a method of adjusting the motor control signal according to an embodiment of the present invention. In operation 301, a sensor output signal is received, such as by a processor. In operation 302, a processing time of the sensor output signal and a motor control signal is calculated. In addition, an amount of time necessary to process the sensor output signal and generate a motor control signal based on the sensor output signal is calculated. In one embodiment, calculating the processing time includes measuring a time with a timer, and in another embodiment, calculating the processing time includes retrieving pre-stored processing time calculations, averages, or representative values stored in memory.

In operation 303, an adjusted motor control signal is generated based on the calculated processing time. In other words, embodiments of the present invention may take into account that by the time a motor control signal is generated in response to a sensor output signal, a characteristic of a rotor detected by a sensor as indicated by the sensor output signal may have changed. For example, if a sensor senses a position of a rotor, the position may be different from the sensed position by the time a motor control signal is generated in response to the sensed position. Accordingly, embodiments of the present invention adjust the motor control signal to correspond for an extrapolated characteristic of the rotor at a time of generating the motor control signal, rather than at the time of sensing the rotor characteristic.

Accordingly, embodiments of the present invention provide rotation direction information of a rotor by detecting a direction from which a rotor feature enters a sensing zone, resulting in a motor control unit requiring less processing time or fewer hardware components than motor control units that require other means to detect the position of a rotor. In addition, embodiments of the present invention provide for accurate control of a motor by adjusting output motor control signals to account for processing time of sensing signals on which the motor control signals are based.

Embodiments of the present invention may be directed particularly to small motors, rotors, and motor control units. Examples of small motors and rotors include motors and rotors of a size small enough to fit in a joint of a human prosthetic limb, such as approximately 1 cm or less in diameter. In prosthetic limbs and other environments having limited space and a need for highly accurate motor control signals, embodiments of the present invention provide for accurate measurements of motor or rotor position and accurate control of a motor while maintaining a small component volume.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated The flow diagrams depicted herein provide examples of processes of exemplary embodiments of the present invention. There may be many variations to the processes or the steps (or operations) described therein without departing from the scope of the invention. For instance, the operations may be performed in a differing order or operations may be added, deleted or modified. All of these variations are considered a part of the claimed invention.

While a preferred embodiment of the invention has been described, it will be understood that those skilled in the art may make various improvements and enhancements which fall within the scope of the claims which follow.

What is claimed is:

1. A small motor controller (SMC) system, comprising:
   a motor configured to control a position of a rotor;
   a sensor configured to detect position information of the rotor by detecting a feature on the rotor, the sensor including a detection zone having a first side and a second side; and
   a motor control unit configured to determine a position of the rotor corresponding to one of the first side of the detection zone and the second side of the detection zone based on whether the feature on the rotor is detected crossing the first side or the second side, respectively.

2. The SMC system of claim 1, wherein the sensor is a Hall-effect sensor.

3. The SMC system of claim 1, wherein the feature on the rotor comprises a magnet.

4. The SMC system of claim 1, wherein the motor is located in a joint of a prosthetic device.

5. The SMC system of claim 1, wherein the motor control unit is configured to receive a sensor output signal, calculate a time for processing the sensor output signal, and adjust an output motor control signal based on the calculated time for processing the sensor output signal.

6. The SMC system of claim 5, wherein adjusting the output motor control signal includes adjusting a first output motor control signal corresponding to a first position of the motor to correspond to a second position of the motor based on the calculated time for processing the sensor output signal.

7. A non-transitory, tangible computer-readable medium having stored thereon a computer program, which, when executed by a computer, performs a method on the computer, the method comprising:
   receiving a sensor output signal;
   determining whether the sensor output signal corresponds to a feature of a rotor entering a detection zone of a sensor from a first side or a second side opposite the first side; and
   determining a position of the rotor corresponding to one of the first side of the sensing zone and the second side of the detection zone based on whether the feature on the rotor is detected adjacent to the first side or the second side, respectively.

8. The non-transitory, tangible computer-readable medium of claim 7, wherein the method further comprises:
   calculating a time for processing the sensor output signal and adjusting an output motor control signal based on the calculated time for processing the sensor output signal.

9. A prosthetic limb, comprising:
   a joint including a motor to bend the joint;
   a sensor configured to detect position information of the motor by detecting a feature on a rotor of the motor, the sensor including a detection zone having a first side and a second side; and
   a motor control unit configured to determine a position of the rotor corresponding to one of the first side of the detection zone and the second side of the detection zone based on whether the feature on the rotor is detected crossing the first side or the second side, respectively.

10. The prosthetic limb of claim 9, wherein the sensor is a Hall-effect sensor.

11. The prosthetic limb of claim 9, wherein the feature on the rotor comprises a magnet.

12. The prosthetic limb of claim 9, wherein the motor control unit is configured to receive a sensor output signal, calculate a time for processing the sensor output signal, and adjust an output motor control signal based on the calculated time for processing the sensor output signal.

13. The prosthetic limb of claim 12, wherein adjusting the output motor control signal includes adjusting a first output motor control signal corresponding to a first position of the motor to correspond to a second position of the motor based on the calculated time for processing the sensor output signal.

14. A method comprising:
   receiving a sensor output signal;
   determining whether the sensor output signal corresponds to a feature of a rotor crossing a detection zone of a sensor at a first side or a second side opposite the first side; and
   determining a position of the rotor corresponding to one of the first side of the detection zone and the second side of the detection zone based on whether the feature on the rotor is detected crossing the first side or the second side, respectively.

15. The method of claim 14, further comprising:
   calculating a time for processing the sensor output signal and adjusting an output motor control signal based on the calculated time for processing the sensor output signal.

16. The method of claim 15, wherein adjusting the output motor control signal includes adjusting a first output motor control signal corresponding to a first position of the motor to correspond to a second position of the motor based on the calculated time for processing the sensor output signal.

* * * * *